Figure 1:
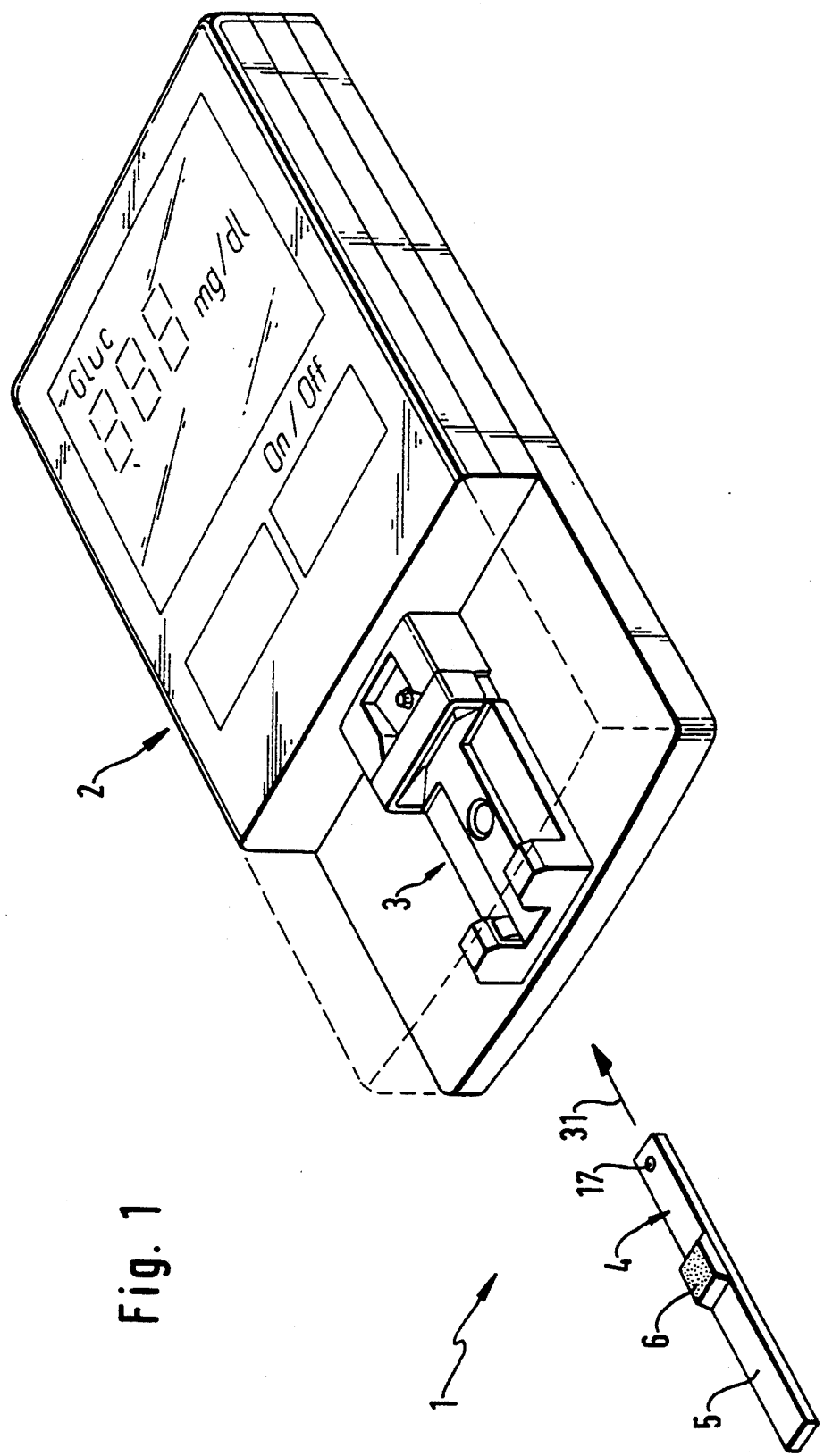

United States Patent [19]
Hönes et al.

[11] Patent Number: 5,424,035
[45] Date of Patent: Jun. 13, 1995

[54] TEST STRIP ANALYSIS SYSTEM

[75] Inventors: Joachim Hönes, Zwingenberg; Volker Unkrig, Ladenburg; Klaus-Dieter Steeg, Kronau, all of Germany

[73] Assignee: Boehringer Mannheim GmbH, Mannheim, Germany

[21] Appl. No.: 219,479

[22] Filed: Mar. 29, 1994

[30] Foreign Application Priority Data

Mar. 31, 1993 [DE] Germany .................. 43 10 583.1

[51] Int. Cl.⁶ ............................................. G01N 21/01
[52] U.S. Cl. ........................................ 422/55; 422/56; 422/68.1; 422/82.05; 436/169
[58] Field of Search ............... 422/55, 68.1, 82.05, 422/56, 58; 436/165, 169

[56] References Cited

U.S. PATENT DOCUMENTS

| | | | |
|---|---|---|---|
| 4,780,283 | 10/1988 | Meinecke et al. | 422/58 X |
| 4,934,817 | 6/1990 | Gassenhuber | 422/68.1 X |
| 5,091,154 | 2/1992 | Pauli et al. | 422/82.05 X |
| 5,211,914 | 5/1993 | Vogel et al. | 422/55 X |
| 5,232,668 | 8/1993 | Grant et al. | 422/82.05 |
| 5,281,395 | 1/1994 | Markart et al. | 422/82.05 |
| 5,316,727 | 5/1994 | Suzuki et al. | 422/82.05 X |

FOREIGN PATENT DOCUMENTS

| | | |
|---|---|---|
| 0183524 | 6/1986 | European Pat. Off. |
| 0319922 | 6/1989 | European Pat. Off. |
| 0333099 | 9/1989 | European Pat. Off. |

*Primary Examiner*—Jeffrey R. Snay
*Attorney, Agent, or Firm*—Nikaido, Marmelstein, Murray & Oram

[57] ABSTRACT

Test strip analysis system includes an analysis apparatus with a test strip holding device (3) and matching test strips. The test strip holding device (3) serves to position the test strip (4) in a defined position relative to a measuring unit (11). It includes a test strip seating device (20) and a guide for the test strip. Exact positioning with simple handling and without sophisticated mechanical elements is achieved by the fact that at least one part of the test strip seating device (20), in the area in which, in the measuring position, the front section (12) of the test strip is located, is formed as a support (24) which is offset in height relative to the middle plane (22) of the test field area (13). The test strip holding device (3) includes a pressure element (33) which, in the measuring position presses between the support (24) and the test field area (13) of the test strip (4) against the side (34) opposite the seating device (20) of the latter. The test strip (4) is consequently subjected to bending stress, whereby the particular distance of the at least one test field (6) from the measuring unit (11) is ensured.

11 Claims, 4 Drawing Sheets

TEST STRIP ANALYSIS SYSTEM

The invention relates to a test strip analysis system which consists of test strips and a test strip analysis apparatus. The analysis apparatus has a test strip holder for positioning the test strip in a defined measuring position relative to a measuring unit. The test strips forming part of the system each have a front end, which generally is first inserted into the test strip holder, and a handling end. A test field area with at least one test field is located between the handling end and the front end. The part of the strip between the test field area and the front end is designated the front section, and the part between the test field area and the handling end is designated as the handling section.

Test strip analysis systems are frequently used for the analysis of fluids, in particular body fluids such as blood or urine. Single-parameter systems, with which only one particular analysis (for example glucose in the blood) can be carried out, may be distinguished from multi-parameter systems which operate with several different types of test carriers, each designed for one analysis, which are all analysed with the same apparatus.

The test strips are usually composed of an elongate base layer and at least one test field arranged thereon. The test field contains one or more reagents. When it is contacted with the sample, a reaction takes place which leads ultimately to a detectable signal, in particular to a colour change in a detection layer. A reflection-photometric measurement in the analysis apparatus, by which the diffuse reflectivity of the test field surface is measured, allows the determination of the concentration of a particular fluid component (analyte).

In order to impose a particular direction on the test strip during the insertion process and to ensure lateral positioning in the measuring position, the test strip holder comprises a guide. Positioning means are provided for the exact positioning of the test strips relative to the reflection photometer. The accuracy of the measurement and the ease of handling are to a substantial extent determined by the positioning device. The positioning of the test strip in the test strip holder refers to three dimensions in space, namely to the longitudinal and lateral directions of the test field surface and to the direction vertical to the test field surface.

The vertical distance of the surface of the test field from the optical measuring system is a critical parameter for an exact measurement. Since (for cost reasons) there is a growing tendency to reduce the area of the test layers, the longitudinal and lateral positioning of the test strips must also be achieved with good precision, so that as large a part as possible of the surface of the detection layer can be used as a measurement area. Incorrect spatial alignment of the test strips causes a reduction in the measurement area and hence measurement errors.

A test strip analysis system of the kind described above is known from EP-A 0 376 111 (U.S. Pat. No. 5,091,154), in which the test strips have a recess in the vicinity of their front end. The positioning device of the analysis apparatus has a pivoted conical cam, which on the insertion of the test strip into the analysis apparatus is swivelled into the recess. In its final position the test strip butts with its front end against a stop and the swivelling conical cam presses it down on to a contact surface. In so doing the cam engages with the recess in such a way that the test strip is subjected to pressure in all three spatial directions, whereby positioning is achieved.

In a further device, known from EP-A 0 129 220 (U.S. Pat. No. 4,780,283), the test strips have recesses at both their handling and front ends, into which a dowel pin engages. During the positioning operation the dowel pin at the front end is first moved into the corresponding recess. The test strip is then bent by the operation of an adjustable flap, so that the dowel pin located in the area of the handling end engages in the second recess. A spring engages with the second dowel pin in such a way that the test strip is under tensile stress in the longitudinal direction. Due to this tensile stress the test strip is pressed with its underside against a pressure plate, as a result of which the test field arranged on the top side of the test strip is in the desired position.

Thus in the known test strip analysis systems a rather complex design with mechanical parts subject to wear has been used for positioning the test strips. In addition it is necessary for the proper functioning of the known devices to position the recesses in the test strips in an exact manner.

The problem addressed by the present invention is therefore to permit precise positioning of the test strips relative to a measuring unit in the analysis apparatus with simple and reliable handling, and to achieve this with an inexpensive design.

This problem is solved according to the invention by means of a test strip analysis system, comprising an analysis apparatus with a test strip holder for positioning a test strip in a defined measuring position relative to a measuring unit, and test strips with a front end with which they are inserted into the test strip holder, a handling end, a test field area with at least one test field between the handling end and the front end, a front section between the test field area and the front end and a handling section between the test field area and the handling end, the test strip holder comprising a guide by means of which a test strip, on insertion into the test strip holder, is guided in its lateral direction, comprises a fixing element which engages in the measuring position with a recess in the test strip, and comprises a test strip seat on which a first side of the test strip rests in such a way that its test field area is at a particular distance from the measuring unit, wherein the test strip holder, in the range in which, in the measuring position, the front section of the test strip is located, comprises a support which is raised against the first side of the test strip so that it is offset in height (in the direction away from the test strip seat) relative to the middle plane of the test field area together with a pressure element which in the measuring position presses between the support and the test field area against the second side of the test strip, so that the test strip in the measuring position is subject to bending stress, whereby a defined distance of the at least one test field from the measuring unit is ensured.

In the context of the invention it has been found that bending of the test strip about a bending axis oriented transversely to its longitudinal axis and parallel to its surface may be used for the positioning. The bending stress is due to the elasticity of the base layer of the test strip. All analysis elements (test carriers) which by virtue of their material properties and dimensions have sufficient elasticity for such a positioning are therefore to be regarded as test strips for the purpose of the invention. The bending stress is generated mainly in the front section, while the handling section is generally unstressed.

In the case of the test strip analysis system according to the invention, positioning and fixing of the test strip in a defined measuring position is achieved simply by the insertion movement of the test strips into the test strip holder. No mechanism for fixing the test strips in the analysis apparatus has to be operated either by the user or by a drive of the analysis apparatus.

It is of particular advantage that exact positioning of the test field is achieved without any parts pressing downwards on to the test strip in the vicinity of the test field area. In previously known apparatuses the test strip holder is in many cases located beneath a flap with retaining springs which press downwards on to the test strips. The opening and closing of this flap is an additional handling step and a possible source of errors if the flap is inadvertently not closed completely. In order to avoid the need for a pressure element in the vicinity of the test field in a further known apparatus grooves are provided, in which the sides of the test strip are guided. In order to ensure in such a design good accessibility of the test field for the application of blood, extremely wide test strips are required, with a relatively small test field in the centre of the test strip width. This results in higher manufacturing costs and a greater packaging volume.

The invention allows very good accessibility of the test field and precise positioning at extremely low cost, as regards both the test strip holder and the test strips themselves.

In a preferred embodiment the fixing element is a stationary protruding element (hereafter designated "retaining lug") with a lateral surface on which at least a part of the edge of the recess in the test strip rests. The lateral surface forms an acute angle with the test strip surface (in the area of the recess). Thus the inclined lateral surface of the retaining lug forms the support.

In a first variant of this embodiment the shape and size of the recess in the test strip and the shape and size of the retaining lug are coordinated with one another so that the edge of the recess rests in the measuring position on at least two points on the lateral surface of the retaining lug, so that the test strip is fixed against axial movements both in the direction to its handling end and to its front end.

In this variant no stop is required at the front end of the test strip seat. For exact positioning only the tolerance of the distance between the test field and the recess has to be small. This is easy to achieve, in particular with so-called "non-wipe" test strips, in which the body fluid flows through the test field from top to bottom and the base layer of the test strip comprises a measuring window through which the diffuse reflectance of the test field is measured reflection-photometrically from its underside. During the manufacture of the test strip the measuring window and the recess in the base layer can be punched out simultaneously in one operation by a suitable tool.

In a second variant of the embodiment with retaining lug the distance between the retaining lug and a stop provided at the front end of the test strip seat and the distance between the front end of the test strip and the section of the edge of the recess in the test strip which faces the front end are coordinated with one another so that the test strip butts in the measuring position with its front end against the stop and rests with the section of the edge of the recess which faces the front end on the inclined lateral surface of the retaining lug. In this case only the distance of the test field from the front end has to be exact. The tolerance on the distance of the recess from the front end may be relatively high in comparison.

In a further preferred embodiment the pressure element is stationary. Thus the test strip holder has no moving parts at all.

Figure 2:
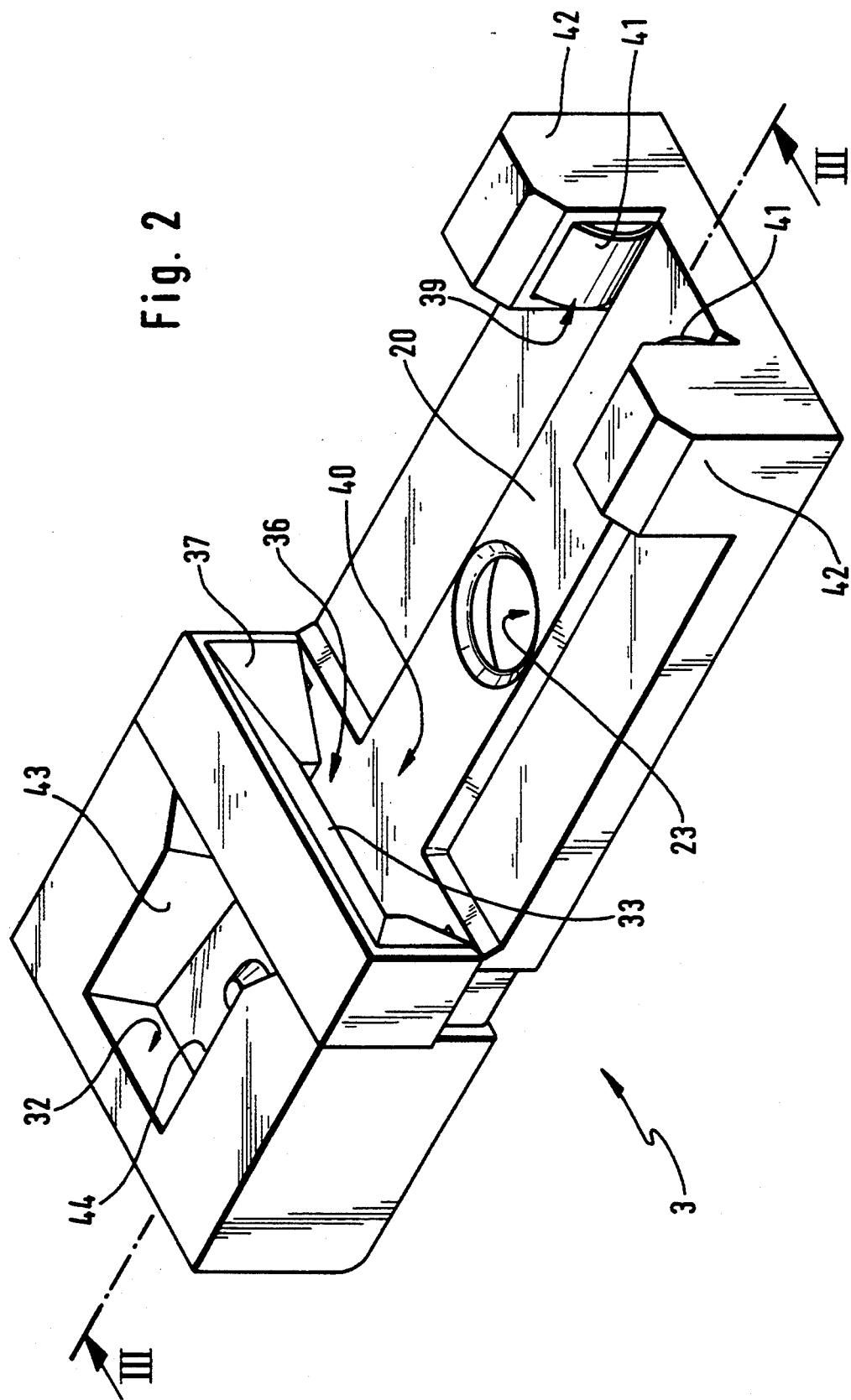
Figure 3:
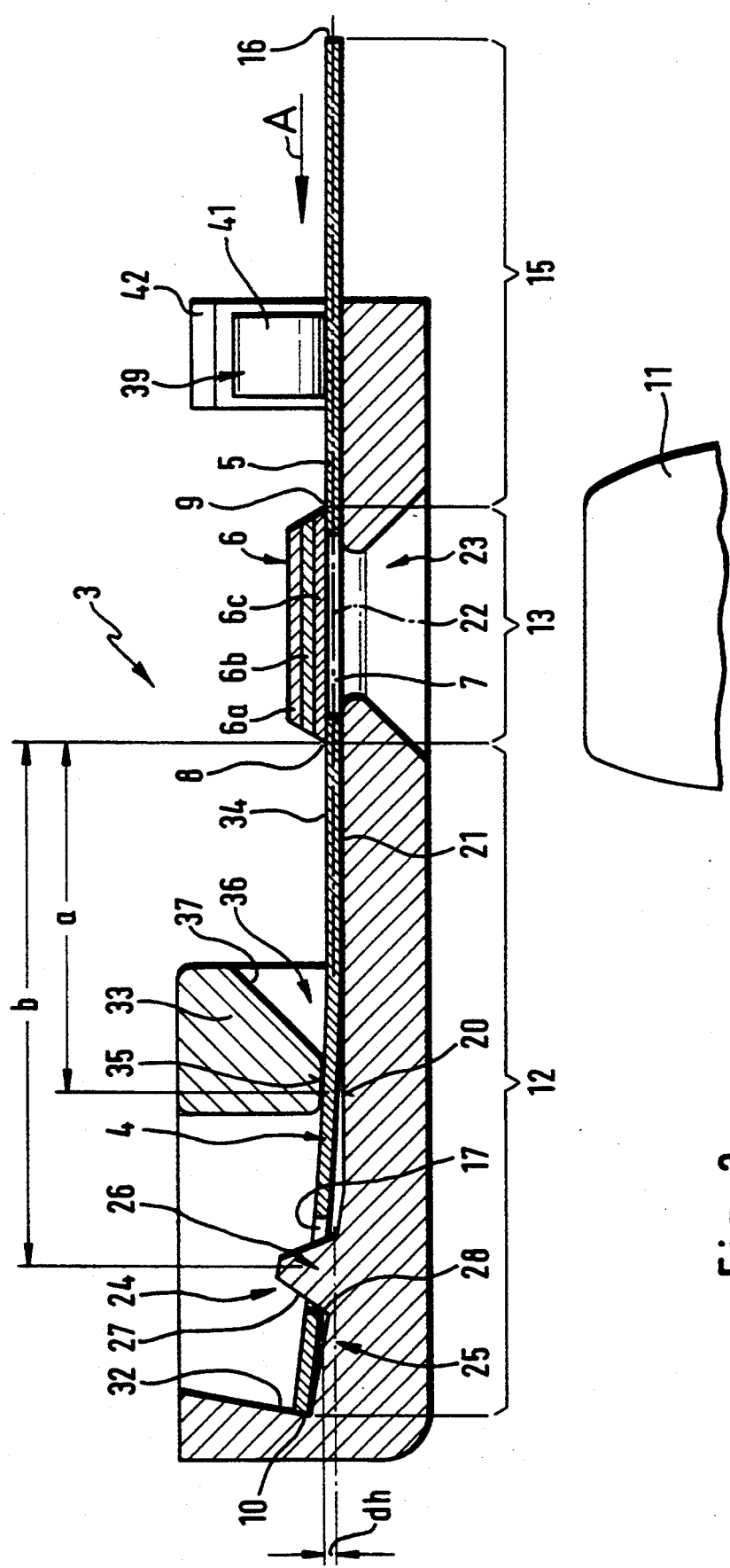
Figure 4:
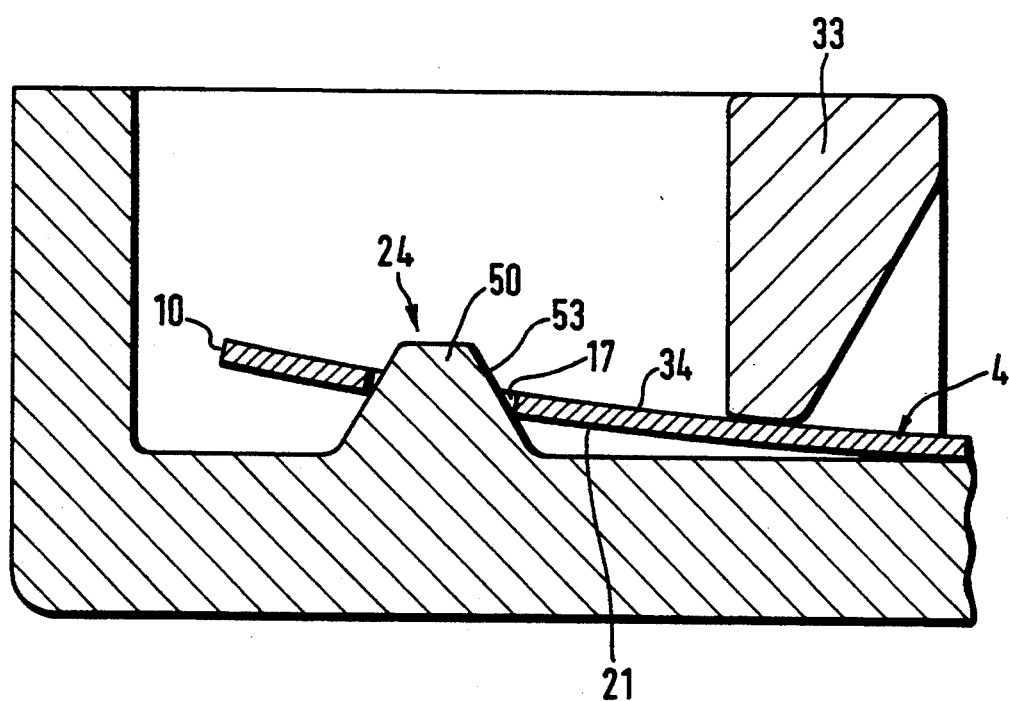

The invention will be described in detail below by means of exemplifying embodiments shown diagrammatically in the figures, where FIG. 1 shows a perspective view of a test strip analysis system according to the invention, FIG. 2 shows a perspective view of a test strip holder, FIG. 3 shows a cross-sectional view along the line III—III in FIG. 2 of a test strip holder with a test strip in the measuring position, and FIG. 4 shows a section of a second variant of the test strip holder in a cross-sectional view according to FIG. 3.

FIG. 1 and FIG. 3 show a test strip analysis system 1, which comprises an analysis apparatus 2 with a test strip holder 3 and test strips 4. The test strips 4 (only one of which is shown) comprise a flexible base layer 5, which usually consists of a plastic material, and a test field 6. The test strip 4 shown is a so-called "non-wipe" test strip. With these test strips the body fluid, after it has been applied to the top side of the test field, passes through the entire thickness of the test field 6 consisting of a plurality of layers 6a–6c (FIG. 3). In so doing chemical reactions take place between the body fluid and the reagents contained in the test field 6. An optically detectable change in a detection layer 6c which results from these reactions may be detected reflection-photometrically from the underside 21 of the test strip. As can be seen in FIG. 3, the base layer 5 of the test strip 4 has for this purpose a measuring opening 7 in the area of the test field 6.

The test strip 4 may in its longitudinal direction be subdivided into three sections. The test field 6 defines a test field area 13. Since the test strip 4 shown comprises only one test field 6, the test field area 13 is bounded by the front edge 8 and rear edge 9 of the test field 6. The invention is however also suitable for test strips in which a plurality of test fields are arranged one behind the other in a larger test field area. In such a case the test field area extends from the front edge of the first test field in insertion direction A to the rear edge of the last test field. The section between the front end 10 (with which the test strip is inserted into the test strip holder 3) and the test field area 13 is described as the front section 12. A handling section 15 extends between the handling end 16 of the test strip 4 (which lies opposite the front end 10) and the test field area 13. In the front section 12 in the vicinity of the front end 10 the test strip 6 comprises a circular-shaped recess 17 which is arranged centrally in the lateral direction of the test strip 6.

As can be seen from FIGS. 2 and 3, the test strip holder 3 is provided with a test strip seat 20 on which the test strip 4 rests with a first side (underside) 21. In the measuring position shown in FIG. 3 the test strip 4 is located on the test strip seat 20 in such a way that the middle plane 22 of the test field area 13 is positioned at a defined distance from a measuring unit 11, which is located beneath the measurement opening 23 of the test strip seat 20. The geometric plane passing in the test field area 13 through the middle of the base layer 5 of the test strip 4 is designated as the middle plane 22 of the test field area 13, and shown in FIG. 3.

A part of the test strip seat 20 is, in the area in which the front section 12 is located when in the measuring position, designed as a support 24, which is offset in height relative to the middle plane 22 of the test field area 6. In other words there is a defined vertical distance of the location at which the test strip 4 rests on the support 24 and the middle plane 22. In the embodiment shown a stationary cone-shaped retaining lug 26 serves both as a support 24 and as a fixing element 25 for fixing the position of the test strip 4 in its longitudinal direction, the insertion movement of the test strip 4 being limited by a stop 32.

For this function of the retaining lug 26 it is important that it has a lateral surface 27 inclined towards the stop 32 (running at an acute angle to the test strip surface in the area of the recess 17) and that the test strip seat 20 is so shaped in the area surrounding the retaining lug 26 that the test strip 4 has in its foremost section facing the front end 10 only two defined points of contact, namely that it butts with its front end 10 against the stop 32 and rests with a section 28 of the edge of the recess 17 which faces the front end 10 on the inclined lateral surface 27 of the retaining lug 26. The distance between the centre of the retaining lug 26 and the stop 32 is slightly less than the distance between the centre of the recess 17 and the front end 10 of the test strip 4.

As a result of this design the possibility of the test strip 4 for moving (downward) in the direction towards the test strip seat 20 is limited (in the area of the retaining lug 26) by the support 24 which is formed by the lateral surface 27. The distance of the support 24 from the middle plane 22 of the test field area 13 is marked dh in the figure. The support 24 is in this case therefore offset by dh relative to the middle plane 22.

The test strip holder 3 comprises a stationary pressure element 33 which spans the test strip seat 20 in the manner of a bridge. The height of the gap 36 formed between the stationary pressure element 33 and the test strip seat 20, through which the test strip 4 is passed on insertion into the test strip holder 3, is at least 1.5 times as great as the thickness of the base layer 5. The pressure element 33 presses about in the middle of the front section 12 against the second side (top side) 34 of the test strip 4. The bottom surface 35, with which the pressure element 33 touches the test strip 4, is closer to the middle plane 22 than the support 24, so that the test strip 4 is subject to bending stress when it is in the measuring position. Due to the elasticity of the base layer 5 the test strip is pressed in the test field area 13 against the test strip seat 20 and hence the defined distance of the test field 6 from the measuring unit 11 is ensured. In order to simplify insertion of the test strip 4 into the gap 36, the front end face 37 of the pressure element 33 is designed funnel-shaped.

Due to the elasticity of the base layer 5 and the geometrical relationships described, the front end 10 of the test strip 4 is also pressed downward. This results in a simultaneous longitudinal positioning of the test strip 4, because the recess 17 slides on the inclined lateral surface 27 in the direction of the stop 32 and hence produces (due to the intrinsic elasticity of the base layer 5) a force component in the longitudinal direction of the test strip 4 on to the stop 32.

The distance a of the stationary pressure element 33 from the boundary of the test field area 13 which faces the front end 10 of the test strip 4 preferably amounts to between 0.35 times and 0.65 times the distance b between the boundary of the test field area 13 which faces the front end 10 and the support 24.

As can be seen from FIG. 3, the length of the test strip seat 20 is shorter than the length of the test strip 4, so that only a part of the handling section 15, namely that facing the test field area 13, rests on the test strip seat 20. The other part of the handling section 15 projects freely out of the analysis apparatus 2, which simplifies the handling of the test strip 4.

As shown in FIG. 2, the test strip holder 3 comprises a guide 40 for the insertion of the test strips 4 and for their exact lateral positioning. In the area of the handling section 15 this guide can be variously configured in consideration of the stiffness of the base layer of the test strips. If the base layer is relatively stiff, it is sufficient if the guide prevents transverse movements of the test strips in this area. This can be achieved for example by means of two guide elements with guide surfaces parallel to the insertion direction and rising vertically from the test strip seat, whose distance from one another is slightly more than the width of the test strips.

In the case of relatively thin and hence flexible test strips it may be advantageous for the reliable placement of the test strips on the test strip seat 20 if the guide 40 presses the test strip on to the test strip seat 20 in addition to the lateral guiding. In the case of the exemplifying embodiment shown in FIGS. 1 to 3 a spring element 39 having elastic springs 41 is arranged in the area of the handling section 15 on both sides of guide 40 at the end of the test strip seat 20. These springs are fixed in corresponding holders 42. The springs 41 project in each case with a profile corresponding to a circular segment out of the receivers 42. The smallest distance of springs 41 from one another is above the test strip seat 20. On the level of a test strip lying on the test strip seat 20 the distance between them is slightly less than the width of said test strip. A test strip 4 can thereby be elastically retained and fixed between the elastic springs 41.

In the area of the front section 12 the guide 40 is formed by the lateral walls 43, 44 bounding the test strip seat 20, which rise vertically from the test strip seat 20. Starting from the pressure element 33 the first part of the lateral walls 43, 44 forms a conically-shaped lateral guide and then the walls 43,44 extend to the stop 32 at a constant distance from one another which is slightly larger than the width of a test strip 4.

If a test strip 4 is to be positioned in the analysis apparatus 2, it is inserted with its front end 10 obliquely from above into the gap 36 of the test strip holder 3. During the further insertion movement the front end 10 is lifted by means of the retaining lug 26 raised relative to the test strip seat 20. As soon as the retaining lug 26 engages with the recess 17, the force component described is exerted towards the stop 32, due to the downward-acting elastic stress of the test strip 4 and the oblique inclination of the lateral surface 27 of the retaining lug 26. The test strip 4 slides in the direction of the stop 32 until it has reached the defined measuring position shown in FIG. 3.

The handling end 16 is pressed manually against the resistance of the springs 41 downwards against the test strip seat 20 and is fixed there by the springs 41.

FIG. 4 shows in a cut-out view an alternative second embodiment of the invention. The main difference compared with the embodiment described above is that this test strip analysis system is designed without a stop in the area of the front end. The other features of the embodiment described before are also provided here. The retaining lug 50 and the recess 17 in the test strip 4 are of circular cross-section, so that the test strip 4, when in its measuring position, rests centrally with the edge of the recess 17 virtually entirely on the lateral surface 53 of the retaining lug 50 and hence is fixed on the latter.

In the embodiments shown in FIG. 3 and FIG. 4 the conically-shaped retaining lug 26, 50 simultaneously provide the functions of a support and of a fixing element. Both functions may however also be fulfilled by separate elements. For example, it would be possible to design the test strip seat 20 in FIG. 3 to be curved uniformly upwards in the direction of the stop 32, in order thereby to provide a support which is offset relative to the middle plane 22 of the test field area 13. The fixing in the longitudinal direction could also be provided at another point, for example in the partial section of the handling section 15 which rests on the seat 20, by means of a recess provided there in the test strip and a corresponding fixing device.

We claim:

1. A test strip analysis system, comprising:
   at least one test strip, said at least one test strip including a front end, a handling end, and a test field area disposed between the handling end and the front end, said test field area including at least one test field thereupon, said test strip also having a front section located between the test field area and the front end, and a handling section located between the at least one test field and the handling end, said at least one test strip including a recess therein; said test strip analysis system further comprising
   an analysis apparatus having test strip positioning means for positioning said at least one test strip in a defined measuring position relative to a measuring unit, said measuring unit being adjacent said test field area when said at least one test strip is positioned in the measuring position, said test strip positioning means including
   guide means for laterally guiding said at least one test strip when said at least one test strip is inserted into the test strip positioning means,
   fixing means for engaging with said recess in said at least one test strip, when said test strip is in the measuring position in the test strip positioning means,
   test strip seating means having a first side for seating a first side of the test strip wherein said seating means is so positioned that said test field area has a predetermined distance from the measuring unit, when said test strip contacting said seating means is positioned in the measuring position,
   supporting means for supporting the front section of the test strip, said supporting means being vertically offset relative to a middle plane of the test field area,
   a pressure element disposed opposite said first side of said test strip seating means, said pressure element positioned to press against a second side of the test strip when said test strip is in said measuring position, said pressure element being located between the test field area of said test strip and the supporting means when the test strip is in the measuring position,
   wherein said test strip is subjected to bending stress by contacting at least the supporting means, the pressure element, and the test strip seating means, thereby ensuring the predetermined distance between the test field area and the measuring unit.

2. A test strip analysis system as recited in claim 1, wherein said test strip seating means is configured such that the first side of the test strip is not contacted by any portion of the test strip seating means in an area of the test strip which is disposed between the supporting means and the pressure element.

3. A test strip analysis system as recited in claim 1, wherein the guide means comprises two guide elements, with one of said guide elements disposed adjacent each lateral side of the test strip, and wherein the pressure element is stationary and connects the two guide elements of the guide means, thereby forming a gap between the test strip seating means and the pressure element, and wherein the test strip is inserted through the gap when being inserted into the test strip holding means.

4. A test strip analysis system as recited in claim 1, wherein a distance between the pressure element and a boundary of the test field area facing the front end of the test strip, when the test strip is inserted into the test strip holding means, is between 0.35 and 0.65 times a distance between the front end boundary of the test field area and the supporting means.

5. A test strip analysis system as recited in claim 1, wherein a length of the test strip seating means is less than a length of the test strip, wherein a handling end of the test strip projects beyond an end of the test strip seating means.

6. A test strip analysis system as recited in claim 1, wherein the guide means includes two guide elements, with each of the guide elements disposed to engage a lateral side of the test strip, and wherein each of said guide elements includes elastic spring elements, said elastic spring elements being configured to press against the lateral edges of the test strip in the handling section thereof, to thereby press the test strip against the test strip seating means.

7. A test strip analysis system as recited in claim 1, wherein said fixing means comprises a stationary retaining element, said stationary retaining element having a lateral surface inclined away from said supporting means, wherein, when said test strip is inserted in said test strip holding means, an edge of the recess engages said inclined lateral surface.

8. A test strip analysis system as recited in claim 7, wherein the edge of the recess engages the stationary retaining element such that the test strip is secured against longitudinal movements in a direction toward the handling end and a direction toward the front end.

9. A test strip analysis system as recited in claim 7, wherein said test strip positioning means includes a stop at an insertion end of the test strip seating means, and wherein a distance between the stop and the retaining element and a distance between the front end of the test strip and an edge of the recess closest to the front end are configured such that when said test strip is in the measuring position, the front end of the test strip contacts the stop, and the edge of the recess closest to the front end engages the inclined lateral surface of the retaining element.

10. A method for supporting a test strip in a test strip analysis system, comprising the steps of:

providing an analysis apparatus having test strip positioning means for positioning at least one test strip in a defined measuring position relative to a measuring unit, with the test strip positioning means including guide means for laterally guiding the test strip when the test strip is inserted into the test strip positioning means, and fixing means for engaging with a recess in the test strip when the test strip is in a measuring position in the test strip positioning means, test strip seating means having a first side for seating a first side of the test strip at a predetermined position from a measuring unit, wherein said seating means is so positioned that said test field area has a predetermined distance from the measuring unit when said test strip contacting said seating means is positioned in the measuring position and supporting means for supporting the front section of the test strip, with the supporting means being vertically offset relative to a middle plane of the test field area, and a pressure element disposed opposite said first side of the test strip seating means, with the pressure element positioned to press against a second side of the test strip when said test strip is in said measuring position, with the pressure element being located between the test field area of said test strip and the supporting means when the test strip is in the measuring position;

inserting a test strip into the test strip positioning means, such that the test strip is subjected to bending stress by contacting at least the supporting means, the pressure element, and the test strip seating means, thereby ensuring a predetermined distance between the test field area and the measuring unit, by exerting a force on the test strip in a direction of the test strip seating means.

11. A test strip analysis system as recited in claim 1, wherein said predetermined distance between said test field area and said measuring unit is ensured by a force provided by the bending stress which presses the test strip against the test strip seating means.

* * * * *